United States Patent
Shirai et al.

(10) Patent No.: US 9,758,952 B2
(45) Date of Patent: Sep. 12, 2017

(54) HUMAN BODY DETECTION SENSOR AND AUTOMATIC FAUCET

(71) Applicant: LIXIL Corporation, Koto-ku, Tokyo (JP)

(72) Inventors: Yuki Shirai, Tokyo (JP); Nobuaki Itazu, Tokyo (JP); Hiroyuki Oura, Tokyo (JP); Kenta Tanaka, Tokyo (JP)

(73) Assignee: LIXIL CORPORATION, Tokyo (JP)

( * ) Notice: Subject to any disclaimer, the term of this patent is extended or adjusted under 35 U.S.C. 154(b) by 43 days.

(21) Appl. No.: 14/753,472

(22) Filed: Jun. 29, 2015

(65) Prior Publication Data

US 2015/0299992 A1 Oct. 22, 2015

Related U.S. Application Data

(63) Continuation of application No. PCT/JP2013/006223, filed on Oct. 21, 2013.

(30) Foreign Application Priority Data

Dec. 28, 2012 (JP) .................. 2012-288852

(51) Int. Cl.
 *E03C 1/05* (2006.01)
 *G01V 8/10* (2006.01)
 (Continued)

(52) U.S. Cl.
 CPC .............. *E03C 1/057* (2013.01); *E03D 5/105* (2013.01); *G01N 21/55* (2013.01); *G01S 7/4912* (2013.01);
 (Continued)

(58) Field of Classification Search
 CPC .. E03C 1/057; G01V 8/10; G01V 8/20; E03D 5/105
 (Continued)

(56) References Cited

U.S. PATENT DOCUMENTS

| 2005/0000015 | A1 | 1/2005 | Kaneko |
| 2012/0211086 | A1 | 8/2012 | Huang et al. |
| 2016/0084959 | A1* | 3/2016 | Shirai ................ E03C 1/057 4/623 |

FOREIGN PATENT DOCUMENTS

| CN | 102692277 A | 9/2012 |
| JP | 2003096850 A | 4/2003 |

(Continued)

OTHER PUBLICATIONS

International Preliminary Report on Patentability corresponding to Application No. PCT/JP2013/006223; Date of Mailing: Jun. 30, 2015, with English Translation.

(Continued)

*Primary Examiner* — Tuan N Nguyen
(74) *Attorney, Agent, or Firm* — Cantor Colburn LLP

(57) ABSTRACT

A human body detection sensor includes: a detection decision unit that decides whether a state is a detection state or a non-detection state of a detection target; a specular reflection decision unit that decides whether or not reflected light that is incident onto a line sensor is specularly-reflected light; and a continuation decision unit that decides whether or not a state in which the detection target exists is ongoing, wherein, when specularly-reflected light is detected while a determination is made indicating the detection state, the detection decision unit keeps the result of a determination indicating the detection state without change if the result of the decision by the continuation decision unit indicates that the state is ongoing and changes the determination to a determination indicating the non-detection state if the result of the decision shows any other states.

5 Claims, 8 Drawing Sheets

(51) Int. Cl.

| | | |
|---|---|---|
| *E03D 5/10* | (2006.01) | |
| *G01S 17/48* | (2006.01) | |
| *G01V 8/20* | (2006.01) | |
| *G01S 17/02* | (2006.01) | |
| *G01S 7/491* | (2006.01) | |
| *G01N 21/55* | (2014.01) | |
| *G01S 17/88* | (2006.01) | |

(52) U.S. Cl.
CPC ............ *G01S 17/026* (2013.01); *G01S 17/48* (2013.01); *G01V 8/20* (2013.01); *G01N 2021/557* (2013.01); *G01S 17/88* (2013.01)

(58) Field of Classification Search
USPC ..................................................... 4/623, 668
See application file for complete search history.

(56) References Cited

FOREIGN PATENT DOCUMENTS

| JP | 2005299142 A | 10/2005 |
|---|---|---|
| JP | 2007057424 A | 3/2007 |
| JP | 2012077472 A | 4/2012 |
| JP | 2012078189 A | 4/2012 |
| JP | 2012207468 A | 10/2012 |
| WO | 2012043663 A1 | 4/2012 |

OTHER PUBLICATIONS

Written Opinion of the International Searching Authority corresponding to Application No. PCT/JP2013/006223; Date of Mailing: Dec. 17, 2013.

International Search Report corresponding to Application No. PCT/JP2013/006223; Date of Mailing: Dec. 17, 2013, with English translation.

Extended European Search Report corresponding to Application No. 13867800.8-1812/2940492 PCT/JP2013/006223 ; Date of Mailing: Jul. 1, 2016.

Chinese Search Report corresponding to Application No. 2013800655365; Date of Mailing: Aug. 1, 2016, with English translation.

Japanese Decision to Grant a Patent corresponding to Application No. 2012-288852; Date of Mailing: Jul. 19, 2016, with English translation.

* cited by examiner

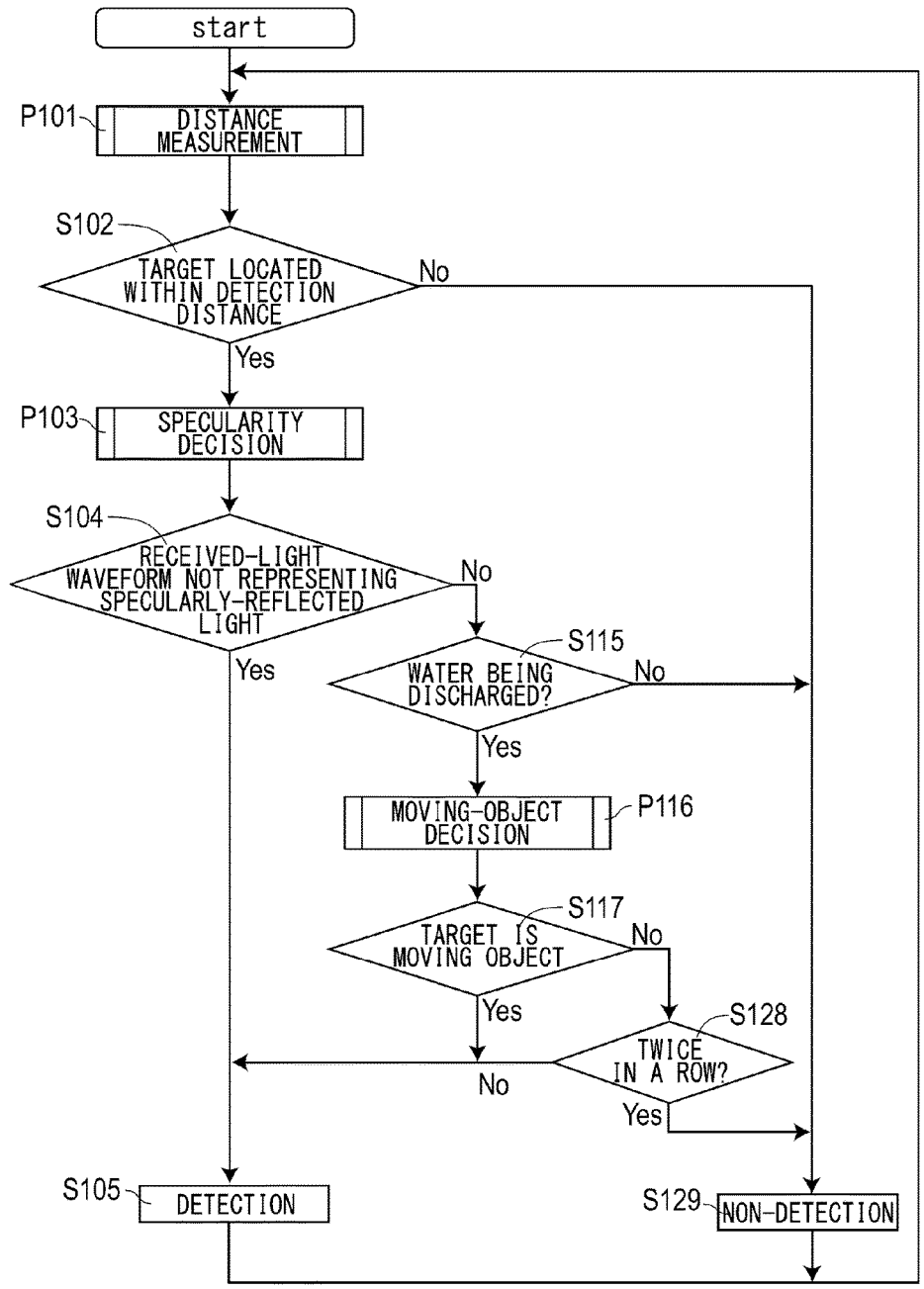

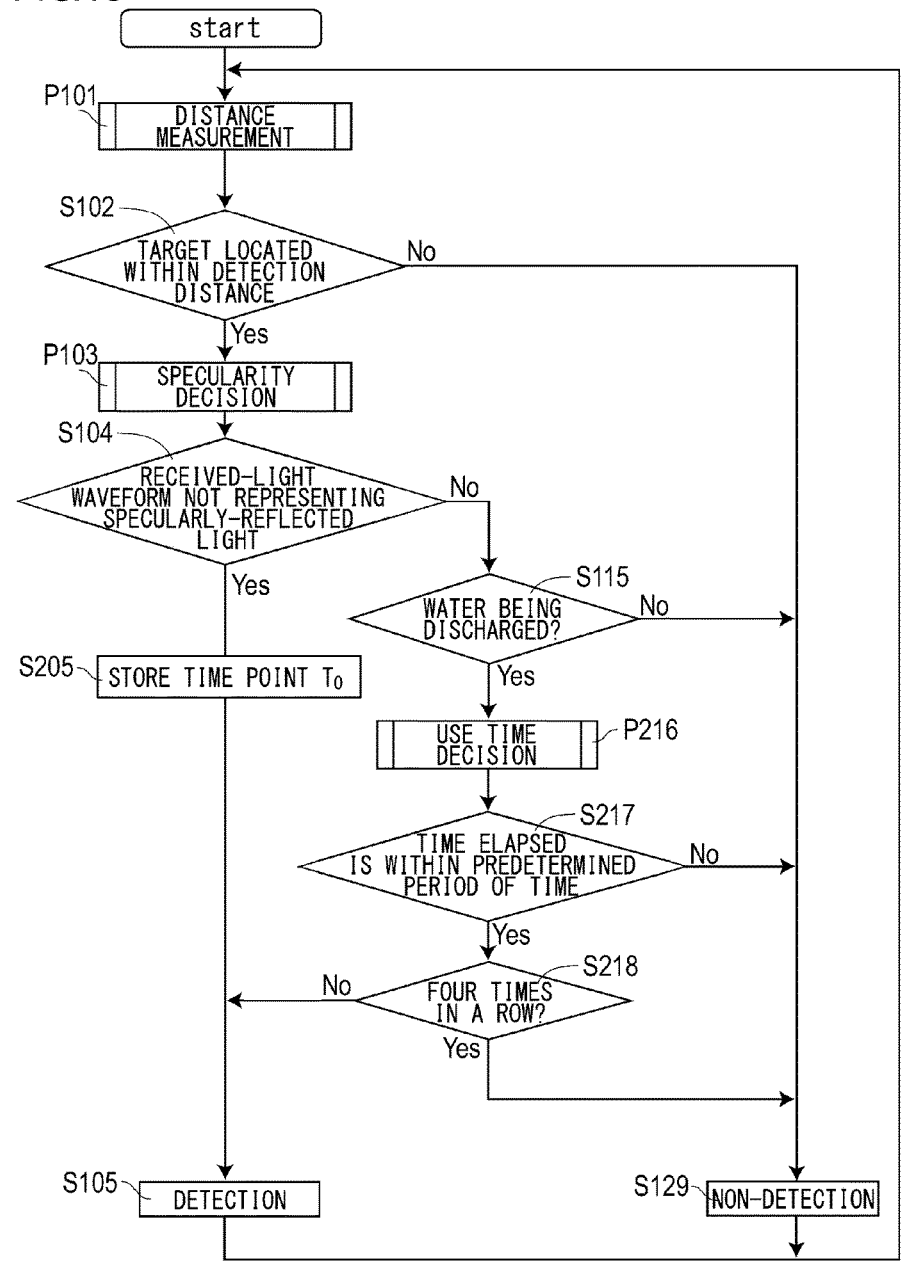

US 9,758,952 B2

HUMAN BODY DETECTION SENSOR AND AUTOMATIC FAUCET

CROSS REFERENCE TO RELATED APPLICATIONS

This application is a continuation under 35 U.S.C. §120 of PCT/JP2013/006223, filed on Oct. 21, 2013, which is incorporated herein reference and which claims priority under 35 U.S.C. §119 to Japanese Application No. 2012-288852, filed Dec. 28, 2012, the entire content of which is also incorporated herein by reference.

FIELD OF THE INVENTION

The present invention relates to a human body detection sensor that is applied to an automatic faucet, an automatic flushing apparatus for a urinal, and the like.

DESCRIPTION OF THE RELATED ART

Automatic faucets that automatically discharge water upon detection of a hand holding-up operation of a user, automatic flushing apparatuses for urinals that automatically provide cleaning water upon detection of a user who has come nearby, and the like are conventionally known. A human body detection sensor for detecting a human body who approaches is incorporated in these automatic faucets, automatic flushing apparatuses, and the like. As such a human body detection sensor, a light-emitting element such as an LED, a light-receiving element such as a position sensitive detector (PSD), and a sensor that is offset-arranged are known.

This human body detection sensor identifies a position where reflected light from a detection target is incident on a PSD and measures a distance to the detection target by the so-called principle of triangulation. A PSD is a very simple light receiving element that output a signal according to the position of the center of gravity of incident light and offers low-power consumption. On the other hand, information that can be acquired by a PSD is positional information only, and there are few coping methods that can be employed when disturbance light is incident. Therefore, for example, in an automatic faucet of a sink where a human body detection sensor including a PSD is used, it is highly difficult to distinguish diffusely-reflected light by a human body surface from specularly-reflected light from a washing bowl. In this automatic faucet, erroneous detection may be caused due to the influence of disturbance light such as specularly-reflected light, and an erroneous operation may occur where water starts being discharged even when nobody is present.

For the purpose of improving detection performance, a human body detection sensor is suggested that uses an imaging element such as a charged coupled device (CCD), a complementary metal oxide semiconductor (CMOS), or the like. A human body detection sensor that uses an imaging element may be able to improve detection performance by, for example, eliminating the influence of disturbance light by using distribution information of a received-light quantity of each pixel or the like. For example, human body detection sensors have been suggested that distinguish specularly-reflected light by using the peak intensity of a distribution waveform of a received-light quantity of each pixel or the shape of the waveform (particularly, kurtosis) and that thereby reduce erroneous detection caused by specularly-reflected light (see, for example, Patent document 1).

[Patent Document 1] Japanese Patent Application Publication No. 2012-77472

In rare cases, specular reflection occurs during the detection of a human body. Thus, if all specularly-reflected light is decided to be erroneous detection, it may be erroneously decided that a detection target is not detected even though the detection target is present. For example, in applications in an automatic faucet or the like, specular reflection can occur by a water surface of water that is being accumulated in both palms in order to wash face, and water may be stopped even during use upon immediate decision indicating that a detection target is not detected.

SUMMARY OF THE INVENTION

The present invention has been made in view of the conventional problems, and a purpose of the invention is to provide a human body detection sensor that properly operates even when specular reflection occurs during the detection of a detection target, and an automatic faucet.

A first embodiment of the present invention relates to a human body detection sensor provided with: an imaging unit that includes an imaging element in which pixels are arranged in a one-dimensional manner or in a two-dimensional manner; and a light-emitting unit disposed with an offset from this imaging unit, in which the imaging unit receives reflected light generated by light projected by this light-emitting unit so as to detect a detection target, including: a specular reflection decision unit that decides whether or not the reflected light is specularly-reflected light; and a continuation decision unit that decides whether or not a state in which the detection target exists is ongoing, wherein, when the reflected light is decided to be specularly-reflected light during the detection of the detection target, a determination indicating detection is kept if the result of the decision by the continuation decision unit indicates that the state is ongoing, and a determination indicating non-detection is made if the result of the decision by the continuation decision unit indicates that the state is not ongoing (claim 1).

A second embodiment of the present invention relates to an automatic faucet including: a faucet that discharges water into a bowl provided with a drainage port at the bottom of the bowl; the human body detection sensor according to the first embodiment; and a water supply control unit that performs the switching of discharging and stopping of water from the faucet by using a sensor signal that is output depending on whether this human body detection sensor is in a detection state or in a non-detection state.

A human body detection sensor according to the present invention includes a specular reflection decision unit that decides whether reflected light is specularly-reflected light; and a continuation decision unit that decides whether or not a state in which the detection target exists is ongoing. In this human body detection sensor, a determination made when a reflected light is decided to be specularly-reflected light under the detection state varies depending on the result of the decision made by the continuation decision unit. If the decision indicates that a state in which the detection target exists is ongoing, the determination indicating the detection is kept. If the decision indicates that the state in which the detection target exists is not ongoing, a determination indicating non-detection is made according to the decision indicating that reflected light is specularly-reflected light. As described, in the human body detection sensor according to the present invention, even when specularly-reflected light becomes incident during the detection of the detection target, a determination indicating non-detection is not made immediately, and an erroneous determination can be prevented before any erroneous determination is made.

As described above, the human body detection sensor according to the present invention and the automatic faucet provided with this human body detection sensor are products with excellent properties that operate properly even when specular reflection occurs during the detection of the detection target.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 14 is a flow diagram illustrating the flow of a detection process by the human body detection sensor in the first exemplary embodiment; and FIG. 15 is a flow diagram illustrating the flow of another detection process in a second exemplary embodiment.

DETAILED DESCRIPTION OF THE INVENTION

A detailed explanation will be given regarding an embodiment of the present invention using the following exemplary embodiments.
(First Exemplary Embodiment)

Figure 1:
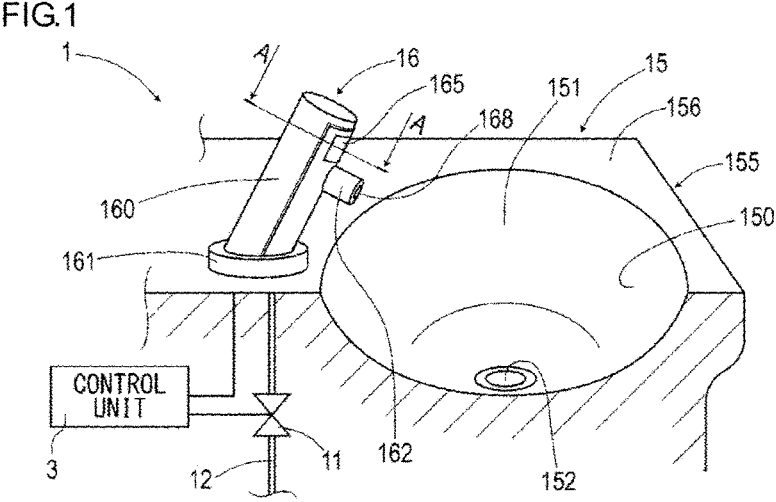
FIG. 1 is a perspective cross-sectional view illustrating a sink provided with an automatic faucet in a first exemplary embodiment.

This exemplary embodiment represents an example where a human body detection sensor 1 is applied to a faucet (automatic faucet) 16 of a sink 15. Regarding the details of this, an explanation will be given in reference to FIGS. 1-15. As shown in FIG. 1, the sink 15 according to the present exemplary embodiment is provided with a counter 155 on which a bowl 151 recessed in a concave shape is provided and the faucet 16 having a water discharge port 168. The faucet 16 is installed in a standing manner on a counter top 156 that forms the upper surface of the counter 155. A drainage port 152 for draining water is disposed at the deepest part of the bottom of the bowl 151.

The faucet 16 has an approximately columnar body portion 160 installed in a standing manner on the counter top 156 and a base portion 161 serving as a pedestal for this body portion 160. The body portion 160 is supported by the base portion 161 in a state where the body portion 160 is inclined toward the bowl 151. An approximately cylindrical water discharge portion 162 is attached to the side of the body portion 160 facing the bowl 151, and the water discharge port 168 is open at the tip of the water discharge portion 162. A filter plate 165 forming a detection surface of the human body detection sensor 1 is arranged on the side surface of the body portion 160 above this water discharge portion 162. The filter plate 165 is a resin-made filter that selectively transmits light in an infrared region. Water is supplied to the water discharge port 168 of the faucet 16 through a water supply channel inside a water supply pipe 12. A water discharge valve (electromagnetic valve) including a solenoid (water supply control unit) 11 is placed in the water supply channel, and the water supply channel is opened and closed by the water discharge valve.

Figure 2:
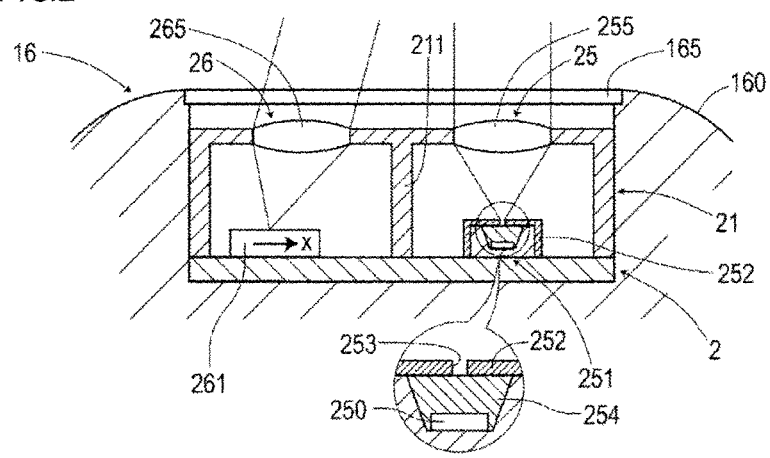
FIG. 2 is a cross-sectional view illustrating a cross-sectional structure of a sensor unit in the first exemplary embodiment (A-A line arrow cross-sectional view in FIG. 1)

As shown in FIGS. 1 and 2, the human body detection sensor 1 according to the present exemplary embodiment comprises a sensor unit 2 incorporated in the faucet 16 and a control unit 3 that controls the sensor unit 2. An automatic water supply apparatus is formed by a combination of this human body detection sensor 1 and the solenoid 11 in the sink 15.

As shown in FIGS. 1 and 2, the sensor unit 2 is a unit where an LED element 251 and a line sensor (imaging element) 261 are housed in a housing 21 and operates when receiving power supply from the control unit 3. In the sensor unit 2, a light-emitting unit 25 and an imaging unit 26 are arranged in parallel facing the filter plate 165 of the faucet 16. The light-emitting unit 25 comprises the LED element 251 and a light projection lens 255. The imaging unit 26 comprises the line sensor 261 and a condenser lens 265. The light-emitting unit 25 and the imaging unit 26 are arranged with an offset in a horizontal direction across a partition 211 having a light shielding property.

As shown in FIG. 2, the LED element 251 is a light-emitting element in which an LED chip 250 mounted in a cavity of a package substrate is sealed by a transparent resin 254. In the light-emitting unit 25, the LED element 251 is covered by an element case 252 having a light shielding property on which a slit hole 253 is provided along a longitudinal direction (in a vertical direction). This light-emitting unit 25 allows sharp slit light whose spread angle in a horizontal direction is reduced to be projected toward a detection target.

Figure 3:
FIG. 3 is a perspective view illustrating a line sensor in the first exemplary embodiment.

As shown in FIGS. 1-3, the line sensor 261 is an imaging sensor in which pixels 260 that convert a received-light quantity into an electrical physical quantity are arranged one-dimensionally. The line sensor 261 has 64 pixels 260 as effective pixels. In the line sensor 261, a light-receiving area 263 is formed by these 64 pixels 260. The line sensor 261 is provided with an electronic shutter (not shown) and is capable of adjusting light-receiving (exposure) time of each of the pixels 260 using this electronic shutter. The line sensor 261 outputs imaging data every time a light-receiving operation is performed. The imaging data according to the present exemplary embodiment is one-dimensional digital data where pixel values of 256 tones that express a received-light quantity are arranged in the order of respective pixels 260.

In the sensor unit 2 according to the present exemplary embodiment, the line sensor 261 is incorporated in such a manner that the longitudinal direction (x direction) of the light-receiving area 263 matches the offset direction of the light-emitting unit 25 and the imaging unit 26. This sensor unit 2 is incorporated in the faucet 16 such that a view of a bowl surface 150, which is an inner circumferential surface of the bowl 151, can be taken by the light-receiving area 263 of the line sensor 261. If there is no shielding object such as a hand in the imaging direction of the line sensor 261, the bowl surface 150 is included in the imaging range thereof.

Figure 4:
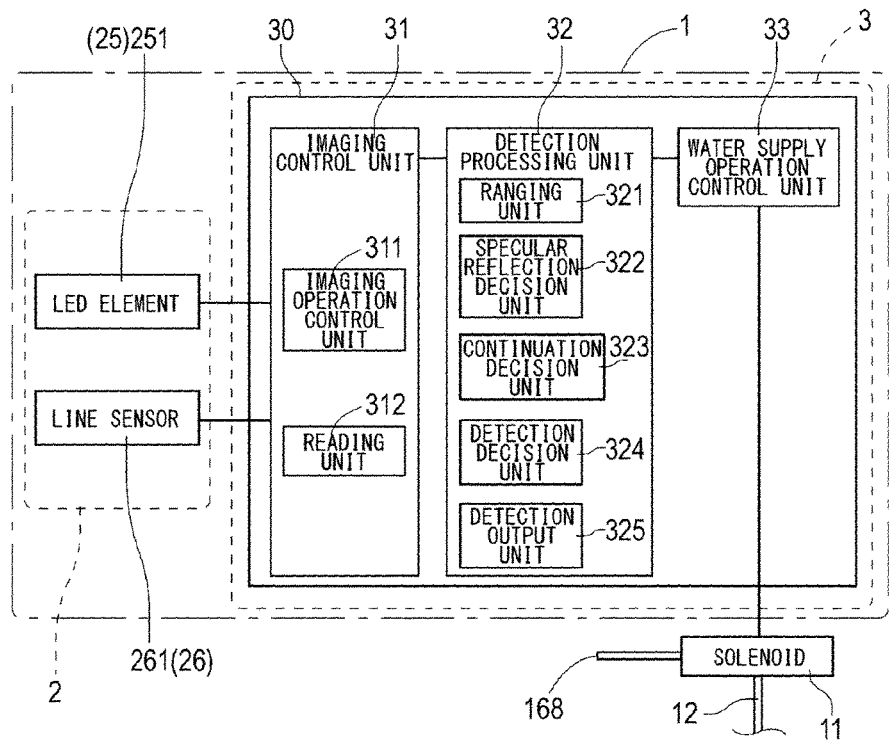
FIG. 4 is a block diagram illustrating a system configuration of a human body detection sensor in the first exemplary embodiment.

As shown in FIGS. 1 and 4, the control unit 3 is a unit that controls the sensor unit 2 and the solenoid 11 and operates by power supplied from a commercial power source. This control unit 3 is provided with a control substrate 30 that controls the sensor unit 2 and the solenoid 11. In the control substrate 30, an imaging control unit 31 that controls the line sensor 261 and the LED element 251, a detection processing unit 32 that performs a detection process, and a water supply operation control unit 33 that controls the solenoid 11 are provided.

The imaging control unit 31 is provided with an imaging operation control unit 311 that controls the LED element 251 and the line sensor 261 and a reading unit 312 that reads out imaging data (a received-light waveform that expresses the distribution of a received-light quantity of each of the pixels 260) from the line sensor 261. The imaging operation control unit 311 controls an imaging operation where the emission of light by the LED element 251 and the receiving of light by the line sensor 261 are performed. In the present exemplary embodiment, the cycle of the imaging operation is set to be about 250 milliseconds. The imaging control unit 31 reads out the received-light quantity of each pixel every time imaging is performed and outputs a received-light waveform just like the one in FIG. 5. A horizontal axis represents a pixel number (pixel position) x, and a vertical axis represents a received-light quantity D(x) in the figure.

The detection processing unit 32 is provided with a ranging unit 321 that performs distance measurement to a detection object, a specular reflection decision unit 322 that decides whether or not reflected light is specularly-reflected light, a continuation decision unit (use decision unit) 323 that decides whether or not an in-use state (a state where a detection object is present) is ongoing, a detection decision unit 324 that determines whether a state is a detection state or a non-detection state, and a detection output unit 325 that outputs a detection signal (sensor signal) under the detection state.

Figure 5:
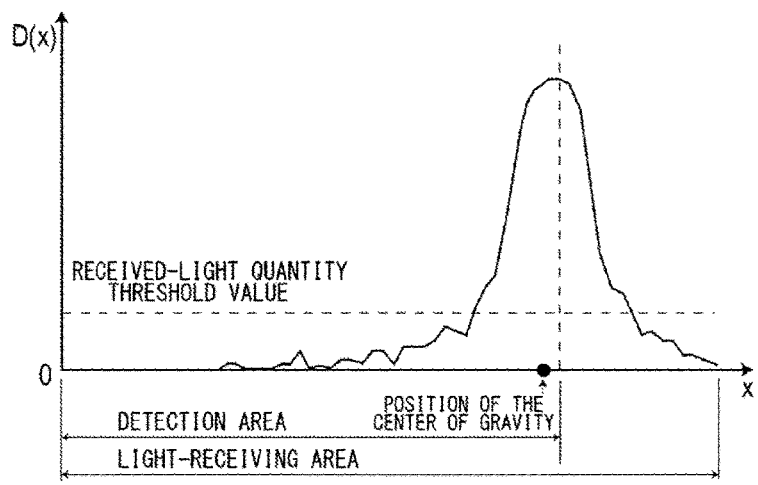
FIG. 5 is a diagram illustrating a received-light waveform by the line sensor in the first exemplary embodiment.
Figure 6:
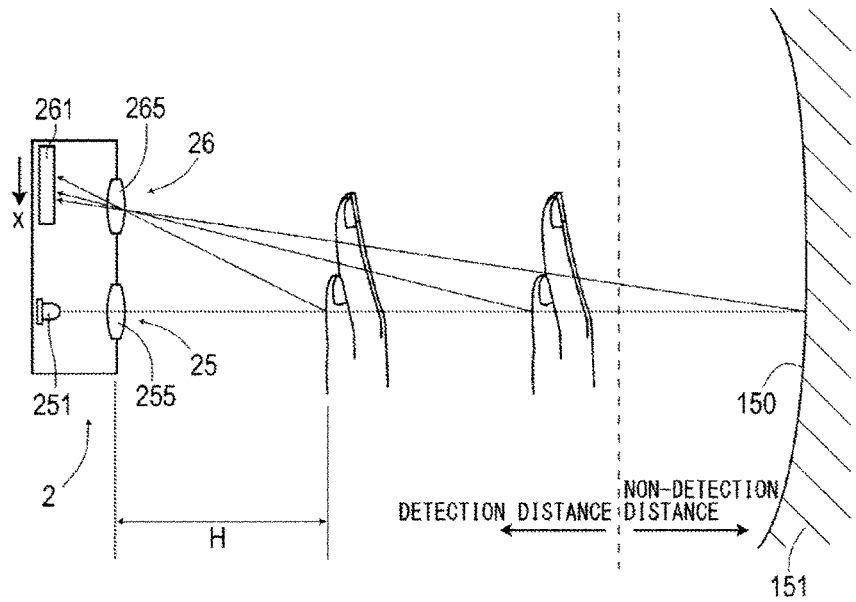
FIG. 6 is an illustrative view explaining a detection principle where a distance is used in the first exemplary embodiment.

The ranging unit 321 measures the position of the center of gravity of a received-light waveform (see FIG. 5) of reflected light from a detection target as a distance index value that indicates a distance. As in FIG. 6 showing a positional relationship of the sensor unit 2, the bowl surface 150, and a user's hand, the incident position of reflected light from the hand, which is a detection target, incident on the line sensor 261 varies depending on a distance H to the hand. The shorter the distance H becomes, the higher the incident position of the reflected light incident on the line sensor 261 becomes. The longer the distance H becomes, the lower the incident position of the reflected light becomes. As described, the incident position of reflected light with respect to the line sensor 261 is proportional to the distance to the detection target and can serve as an index value that indicates the degree of the distance. In the present exemplary embodiment, the position of the center of gravity of a received-light waveform is treated as an incident position. As shown in FIG. 5, a detection area (a predetermined range) is set inside a light-receiving area so as to correspond to a detection distance, and the decision of whether or not the position of the center of gravity falls within this detection area means completely the same as the decision of whether or not a detection target is present in the detection distance in FIG. 6.

Figure 7:
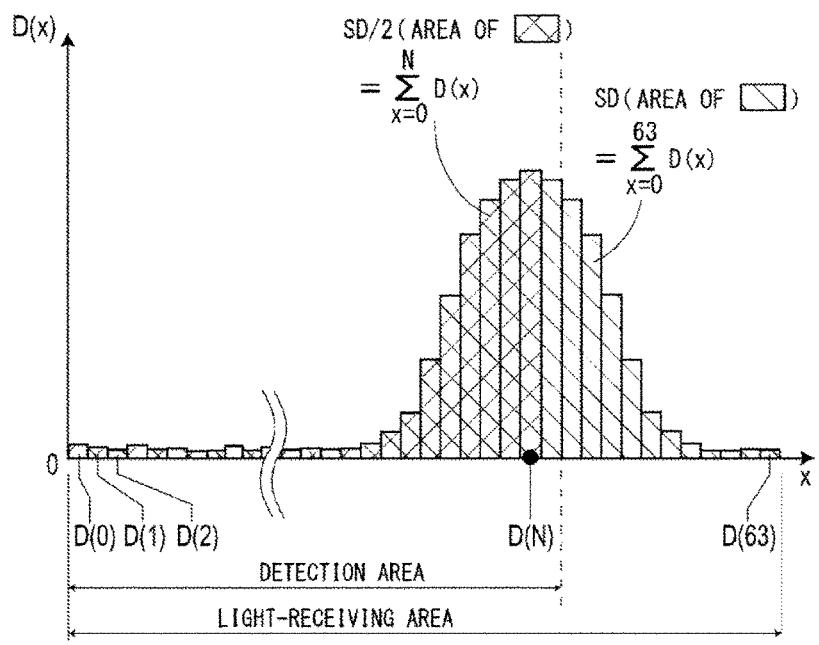
FIG. 7 is an illustrative view explaining a method of calculating the position of the center of gravity in the first exemplary embodiment.

As shown in FIG. 7 schematically indicating the distribution of respective received-light quantities of pixels that constitute this received-light waveform, the ranging unit 321 first integrates received-light quantities D(x) of the respective pixels that constitute the received-light waveform so as to obtain the sum SD of the pixel values of the 64 pixels. The sum SD according to Expression 1 corresponds to the area of a region indicated by hatching with diagonal lines running to the lower right in FIG. 7. The position of the center of gravity of the received-light waveform can be obtained as a pixel position at which a received-light quantity integrated value S(x) according to Expression 2 reaches SD/2, the received-light quantity integrated value S(x) being obtained by the integration of the pixel values of respective pixels 260 performed in order from a pixel on the extreme left in the light-receiving area 263 whose pixel number x is zero.

$$SD = \sum_{n=0}^{63} D(n) \qquad \text{Expression 1}$$

$$S(x) = \sum_{n=0}^{x} D(n) \qquad \text{Expression 2}$$

Figure 8:
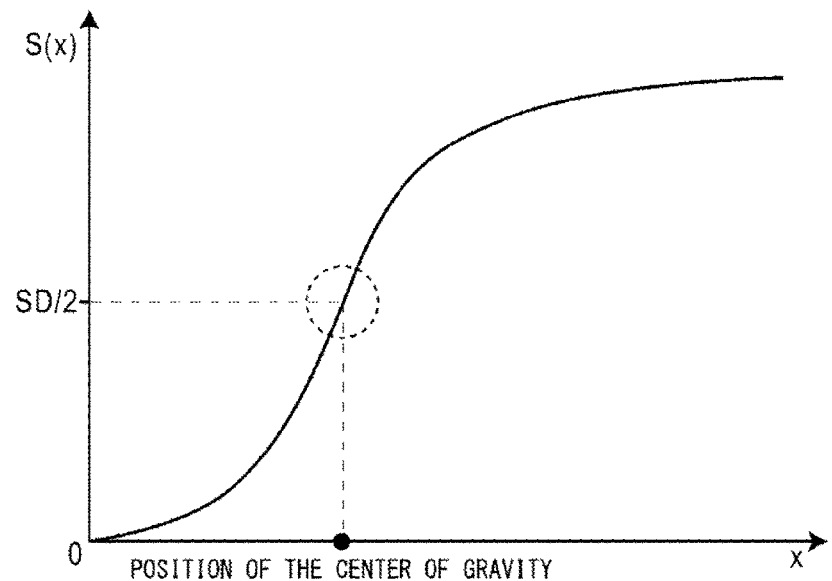
FIG. 8 is a graph illustrating the distribution of an accumulated received-light quantity in the first exemplary embodiment.
Figure 9:
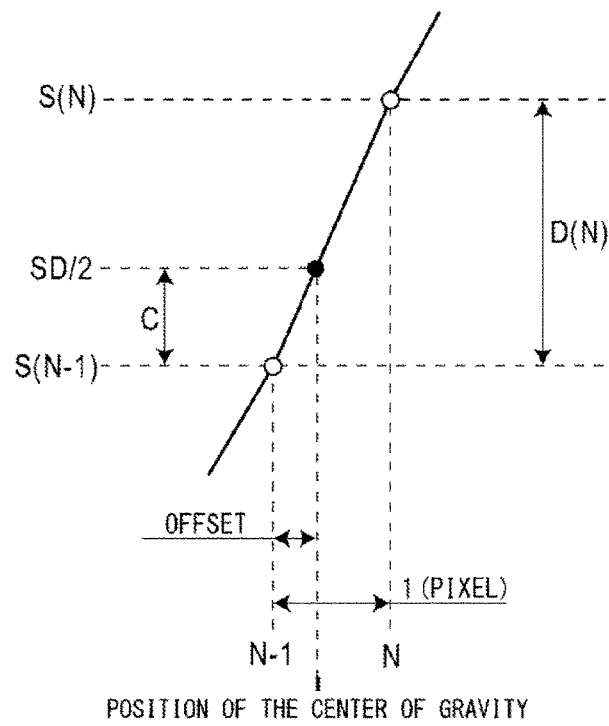
FIG. 9 is an illustrative view explaining a method of obtaining the position of the center of gravity with sub-pixel accuracy in the first exemplary embodiment.
Figure 10:
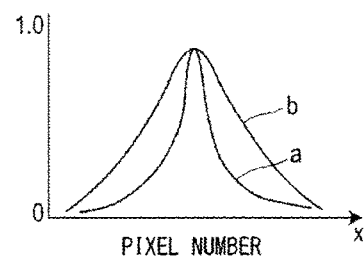
FIG. 10 is a diagram illustrating a difference in a received-light waveform between diffusely-reflected light and specularly-reflected light in the first exemplary embodiment.

As in FIG. 9 where a part in which S(x) becomes SD/2 is enlarged, the ranging unit 321 identifies the position of the center of gravity by using a first pixel (N−1) and a second pixel (N) where a magnitude relationship between S(x) and SD/2 switches in a graph in FIG. 8 showing changes in the received-light quantity integrated value S(x) according to the pixel number x. The ranging unit 321 obtains the position of the center of gravity at which S(x) becomes SD/2 in sub-pixel accuracy of a 1/10 pixel based on the assumption that S(x) changes in a linear manner between S(N−1) with a smaller pixel number and the second pixel (N) with a larger pixel number.

More specifically, a position where the first pixel (N−1) is shifted to the side of the second pixel (N) by an amount of OFFSET (a deviation shown in FIG. 9) according to Expression 4 obtained by transforming a proportional expression according to Expression 3 that is satisfied under an assumption such as the one described above is identified as the position of the center of gravity (the position of a black dot calculated by Expression 5) in sub-pixel accuracy.

$$1 \text{ (PIXEL): OFFSET} = D(N) : C \qquad \text{Expression 3}$$
$$\text{wherein } C = \frac{SD}{2} - S(N-1)$$
$$D(N) = S(N) - S(N-1)$$

-continued $$\text{OFFSET} = \frac{C}{D(N)} \quad \text{Expression 4}$$

$$(\text{POSITION OF THE CENTER OF GRAVITY}) = \quad \text{Expression 5}$$
$$(N-1) + \frac{C}{D(N)}$$

The control unit 3 according to the present exemplary embodiment has a memory area that stores the position of the center of gravity identified by the ranging unit 321. Two previous positions of the center of gravity are stored in this memory area, and the older data is deleted and then rewritten with new data for the position of the center of gravity every time a new position of the center of gravity is identified.

The specular reflection decision unit 322 decides whether reflected light is specularly-reflected light by using the received-light waveform (see FIG. 5) by the line sensor 261. In the present exemplary embodiment, whether reflected light is specularly-reflected light is decided by using a difference in kurtosis that appears remarkably when specularly-reflected light (waveform a in FIG. 10) from the bowl surface 150 and the like and diffusely-reflected light (waveform b in FIG. 10) from a human body surface are normalized by a peak value. As can be known from FIG. 10, while diffusely-reflected light from a detection target such as a human body shows a broad waveform, specularly-reflected light by the bowl surface 150, metallic parts, or the like shows a steep and sharp waveform with a large kurtosis. A horizontal axis represents the pixel number x, and a vertical axis represents ratio of a received-light quantity in the figure.

Figure 11:
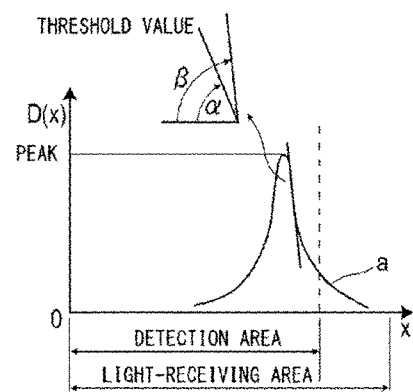
FIG. 11 is an illustrative view of a method of deciding whether reflected light is specularly-reflected light in the first exemplary embodiment.
Figure 12:
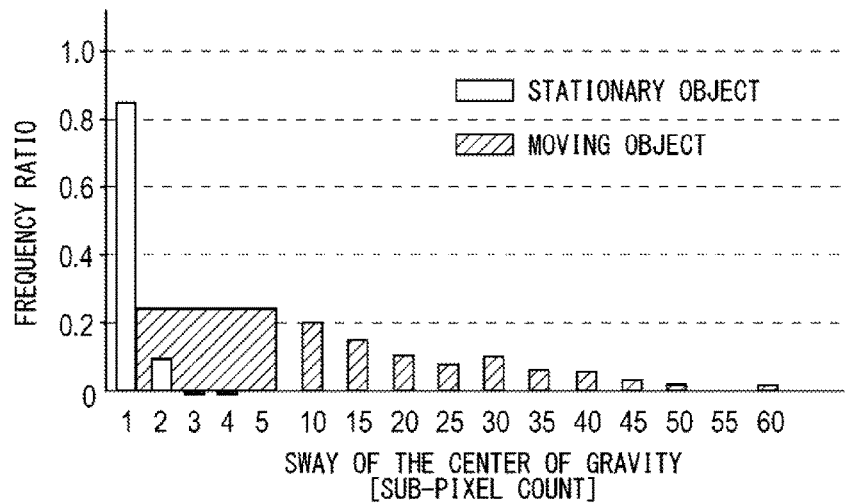
FIG. 12 is a graph illustrating frequency distribution of sway of the center of gravity in the first exemplary embodiment.

More specifically, as in FIG. 11, the specular reflection decision unit 322 according to the present exemplary embodiment sets a threshold value α for the slope steepness of a rise of a waveform toward a peak value and decides that reflected light is specularly-reflected light when the slope steepness β of the rise of the waveform is larger than the threshold value. Instead of this or in addition to this, a threshold value can be set for the slope steepness of a fall of the waveform away from a peak so as to detect specularly-reflected light. A horizontal axis represents the pixel number x, and a vertical axis represents the received-light quantity D(x) in FIG. 11.

Figure 13:
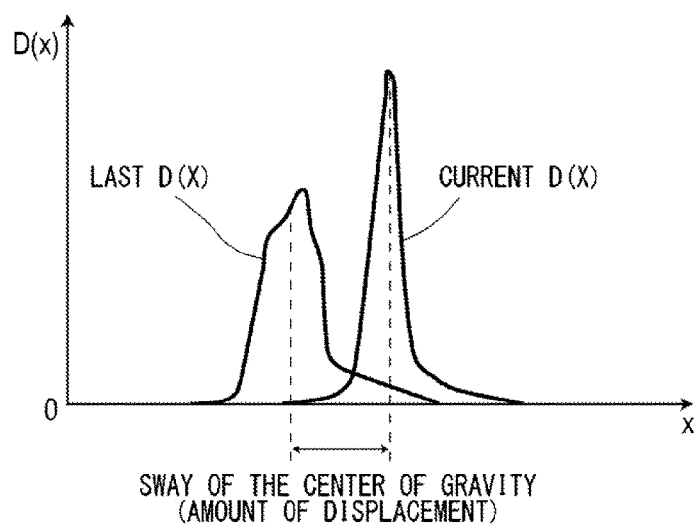
FIG. 13 is a diagram illustrating the sway of the center of gravity in the first exemplary embodiment.

The continuation decision unit 323 detects sway of the center of gravity (a temporal change in the position of the center of gravity of reflected light) identified in sub-pixel accuracy of a 1/10 pixel as described above so as to decide the presence of a moving object and, based on the result of the decision, decides whether or not in-use state is ongoing. In the present exemplary embodiment, a threshold value for moving object decision is set to be five sub-pixels based on experimental knowledge (see FIG. 12) regarding the human body detection sensor 1 according to the present exemplary embodiment where sway of the center of gravity exceeds five sub-pixels in the majority of moving objects while the sway of the center of gravity of reflected light by a stationary object is around one to two sub-pixels. A horizontal axis represents a sub-pixel count, and a vertical axis represents ratio of the frequency of occurrence with respect to the entire frequency in FIG. 12. The continuation decision unit 323 decides, for two received-light waveforms that are temporally continuing as shown in FIG. 13, that there is a moving object when the sway of the center of gravity obtained in sub-pixel accuracy exceeds five sub-pixels and decides that the in-use state is ongoing based on this.

The detection decision unit 324 makes a final determination regarding whether a state is a detection state or a non-detection state by appropriately combining the position of the center of gravity identified by the ranging unit 321, the decision result by the specular reflection decision unit 322, and the decision result by the continuation decision unit 323. The detection output unit 325 starts the outputting of a detection signal, which is a sensor signal, to the solenoid 11 when the detection decision unit 324 determines that the state is a detection state and stops the outputting of a detection signal according to a change in the determination to a non-detection state. Upon receiving the sensor signal from the detection decision unit 324, the solenoid 11 opens the water supply channel so that water is discharged from the faucet 16. On the other hand, when the inputting of the sensor signal from the detection decision unit 324 is stopped, the solenoid 11 closes the water supply channel so that water from the faucet 16 is stopped. As described, the solenoid 11 performs the switching of discharging and stopping of water from the faucet 16 by using the sensor signal output from the detection output unit 325 according to the detection result from the detection decision unit 324 of the human body detection sensor 1.

Next, an explanation will be made regarding the flow of a detection process by the human body detection sensor 1 according to the present exemplary embodiment configured as described above in reference to a flow diagram in FIG. 14. In the detection process, the control unit 3 first performs a distance measurement process P101 where reflected light from a detection target is used. This distance measurement process P101 is started by a series of imaging operations by the control by the control unit 3. The imaging control unit 31 of the control unit 3 performs the exposure of light (the receiving of light) by the line sensor 261, which is synchronized with the emission of light by the LED element 251, and the exposure of the line sensor 261 with no emission of light in a row and obtains, for each of the pixels, the received-light quantity D(x) for the difference between the two occasions of the receiving of light. According to this series of imaging operations, the received-light waveform illustrated in FIG. 5 where the received-light quantity D(x) for the difference for each of the pixels is distributed can be obtained. In this received-light waveform, the influence surrounding light is suppressed by obtaining the difference in the received-light quantity, and components of reflected light resulting from LED light are extracted with high accuracy.

The ranging unit 321 of the control unit 3 identifies the position of the center of gravity, which is used for a distance index value for a distance to the detection target, in sub-pixel accuracy of a 1/10 pixel on the condition that the received-light quantity D(x) of any of the pixels that form the received-light waveform exceeds a received-light quantity threshold value (see FIG. 5). As described above, the control unit 3 stores data for the two latest positions of the center of gravity, and the control unit 3 deletes the older data for the position of the center of gravity and then performs rewriting with new data when a new position of the center of gravity is identified.

The ranging unit 321 of the control unit 3 uses the position of the center of gravity of reflected light identified as the distance index value so as to perform the decision of whether or not the detection target is located within the detection distance (S102). As described above, by performing the decision of whether or not the position of the center of gravity of the received-light waveform falls in the detection area (see FIG. 5), the ranging unit 321 of the control unit 3 according to the present exemplary embodiment decides whether or not the detection target falls within the detection distance (see FIG. 6).

When the detection target does not fall within the detection distance (S102: NO), the detection decision unit 324 of the control unit 3 determines that the state is the non-detection state (S129). On the other hand, when the detection target falls within the detection distance (S102: YES), the specular reflection decision unit 322 of the control unit 3 performs a specularity decision process P103. The specular reflection decision unit 322 of the control unit 3 performs the determination, for the received-light waveform, of whether or not the slope steepness β of the rise to the peak exceeds the threshold value α that has been set in advance (see FIG. 11) and then decides whether or not the reflected light is specularly-reflected light.

When the reflected light is not specularly-reflected light (S104: YES), the detection decision unit 324 of the control unit 3 determines that the state is the detection state (S105) and then performs a subsequent imaging operation in a cycle of 250 milliseconds. On the other hand, when the reflected light is specularly-reflected light (S104: NO), the detection processing unit 32 of the control unit 3 performs the determination of whether or not water is being discharged (in the detection state) (S115). When water is not being discharged (S115: NO), the detection decision unit 324 of the control unit 3 keeps the determination indicating that the state is the non-detection state (S129). When water is being discharged (S115: YES), the continuation decision unit 323 of the control unit 3 performs a moving-object decision process P116.

In this moving-object decision process P116, determination is made by a threshold value regarding whether or not the difference (sway of the center of gravity) between the last position of the center of gravity stored in the control unit 3 and the newly-identified position of the center of gravity is five sub-pixels or more. The continuation decision unit 323 of the control unit 3 decides that there is a moving object when the temporal difference between the positions of the center of gravity exceeds five sub-pixels and decides that there is no moving object when the difference is five sub-pixels or less.

When the continuation decision unit 323 has decided that there is a moving object (S117: YES), the detection decision unit 324 of the control unit 3 keeps the determination indicating that the state is the detection state (S105) even when the reflected light has been decided to be specularly-reflected light in step S104 (S104: NO). In other words, when reflected light is decided to be specularly-reflected light by the specular reflection decision unit 322 during the detection of a detection target, the detection decision unit 324 keeps the determination indicating the detection if the continuation decision unit 323 decides that the state where the detection target exists is ongoing. On the other hand, when the continuation decision unit 323 has decided that there is no moving object (S117: NO), the continuation decision unit 323 of the control unit 3 performs the determination of whether or not the decision indicating that there is no moving object has occurred twice in a row (S128). If the decision indicating that there is no moving object has not occurred twice in a row (S128: NO), the detection decision unit 324 of the control unit 3 keeps the determination indicating that the state is the detection state regardless of the result of the decision indicating there is no moving object (S105) and then performs a subsequent imaging operation. If the decision indicating that there is no moving object has occurred twice in a row (S128: YES), the detection decision unit 324 of the control unit 3 switches the determination from the determination indicating the detection state to the determination indicating the non-detection state (S129). In other words, when reflected light is decided to be specularly-reflected light by the specular reflection decision unit 322 during the detection of a detection target, the detection decision unit 324 makes a determination indicating non-detection if the continuation decision unit 323 decides that the state where the detection target exists is not ongoing.

As described above, the human body detection sensor 1 included in the automatic faucet 16 according to the present exemplary embodiment has a function of deciding whether or not the in-use state is ongoing in addition to a function of measuring a distance to a detection target and a function of deciding whether reflected light is specularly-reflected light. This human body detection sensor makes a determination regarding the switching to the non-detection state according to the decision of whether or not the in-use state is ongoing, without immediately switching the determination to the determination indicating the non-detection state even when reflected light is decided to be specularly-reflected light under the detection state.

Such an operational specification is extremely effective, for example, in a situation where a user is trying to accumulate water in both palms in order to wash face. This is because, since there is a possibility that specular reflection occurs on the surface of water, water may be stopped in the middle of accumulating water if the state is immediately switched to the non-detection state in response to the incidence of specularly-reflected light. In a situation where water is accumulated in palms as just described, the main reflection surface is very likely to change with time, for example, the direction of specular reflection changes in response to the rippling of the surface of water, diffuse reflection caused by the surface of hands becomes dominant instead of specular reflection, and the like. The human body detection sensor 1 according to the present exemplary embodiment where sway of the center of gravity of reflected light is detected allows for detection of a usage situation such as a situation where water is accumulated in both palms with high accuracy so that the continuation of the in-use state can be decided with high certainty, and an erroneous operation of the faucet 16 can thus be prevented before any erroneous operation happens.

As described above, the automatic faucet 16 according to the present exemplary embodiment is capable of operating properly even when specularly-reflected light is generated during use and is a faucet having excellent properties with few erroneous operations such as stopping of water during use.

When a situation where no moving object is decided to be present while reflected light is decided to be specularly-reflected light has occurred twice in a row, the detection decision unit 324 according to the present exemplary embodiment determines that the reflected light is specularly-reflected light from a stationary object (the processing step in S128 shown in FIG. 14). This number of consecutive occurrences is not limited to two stated in the present exemplary embodiment. The number of consecutive occurrences is preferably set appropriately according to the usage situation or the like. Instead of the number, determination by a threshold value regarding the duration of a similar status may be performed.

The specular reflection decision unit 322 according to the present exemplary embodiment decides whether or not reflected light is specularly-reflected light by using the slope steepness of a received-light waveform (see FIG. 11). The method of deciding whether reflected light is specularly-reflected light is not limited to that described in the present exemplary embodiment. The kurtosis of a received-light waveform may be quantified by the determination by a threshold value regarding a width formed by a pixel group that exhibits a received-light quantity of 50 percent of a peak value so as to decide whether reflected light is specularly-reflected light. In addition, the kurtosis of a received-light waveform may be quantified by a statistic such as standard deviation or the like so as to decide whether reflected light is specularly-reflected light, or the kurtosis may be quantified by a frequency component of a received-light waveform that is extracted by applying Fourier transformation or the like so as to decide whether reflected light is specularly-reflected light.

The continuation decision unit 323 according to the present exemplary embodiment performs a moving-object decision by sway of the position of the center of gravity (the incident position of reflected light) of a received-light waveform. A moving-object decision may be performed by the determination by a threshold value regarding a temporal difference in the received-light waveform illustrated in FIG. 5. A moving-object decision may be performed by the determination by a threshold value regarding a temporal change in the received-light quantity of a pixel corresponding to a detection target.

The ranging unit 321 according to the present exemplary embodiment obtains the position of the center of gravity of a received-light waveform in identifying the incident position of reflected light. Instead of the position of the center of gravity, the position of the peak of the received-light waveform may be identified as an incident position. Further, although the position of the center of gravity is calculated by a simple calculation in the present exemplary embodiment, the position of the center of gravity of a received-light waveform may be calculated in a mathematically rigorous manner if there is a margin in calculation processing capacity.

The present exemplary embodiment represents an example where a human body detection sensor 1 is applied to a faucet 16 of a sink 15. Alternatively, the faucet 16 may be a faucet for a kitchen. Further, the human body detection sensor 1 according to the present exemplary embodiment can be also applied as a sensor for an automatic water supply apparatus for a urinal having an automatic flushing function. Furthermore, the human body detection sensor 1 according to the present exemplary embodiment can be also applied to various automatic apparatuses such as lighting that automatically lights up in response to a hand holding-up operation or a human body, automatic doors, and the like.

In the present exemplary embodiment, the sensor unit 2 and the control unit 3 are formed separately. Instead of this, the sensor unit 2 and the control unit 3 may be formed in an integral manner and housed in the faucet 16. Although the human body detection sensor 1 according to the present exemplary embodiment includes the water supply operation control unit 33, the water supply operation control unit 33 can be formed separately. As long as the imaging unit 26 is capable of imaging reflected light, the imaging unit 26 may include an imaging element in which pixels are arranged in a two-dimensional manner instead of an imaging element in which pixels are arranged in a one-dimensional manner. The water supply control unit 11 is required to be capable of performing the switching of discharging and stopping of water from the faucet 16 by the opening and closing of the water supply channel while using a sensor signal output from the detection output unit 325 of the human body detection sensor 1, and a water discharge valve including a stepping motor or the like may be used instead of a water discharge valve that includes a solenoid. FIG. 4 shows functional blocks that can be implemented by the cooperation of hardware and software. These functional blocks may be implemented in a variety of forms by combinations of hardware and software.

(Second Exemplary Embodiment)

The present exemplary embodiment represents an example where the configuration of a continuation decision unit (reference numeral 323 in FIG. 4) is changed on the basis of a human body detection sensor according to the first exemplary embodiment. Regarding the details of this, an explanation will be given in reference to FIG. 15. The same elements as those explained in the first exemplary embodiment shall be denoted by the same reference numerals, and duplicative explanations will be omitted appropriately. The continuation decision unit according to the first exemplary embodiment makes a decision of whether or not the in-use state is ongoing based on a moving-object decision. On the other hand, when reflected light is decided not to be specularly-reflected light by the specular reflection decision unit 322, the continuation decision unit according to the present exemplary embodiment stores a time point at which a human body is detected and presumptively decides that the in-use state is ongoing during a predetermined period of time (two seconds in the present exemplary embodiment) starting from the time point.

An explanation will be made regarding the flow of a detection process by a human body detection sensor according to the present exemplary embodiment in reference to FIG. 15. An explanation will be made mainly regarding differences from the first exemplary embodiment. When a human body is detected within a detection distance by the ranging unit 321 and reflected light is decided not to be specularly-reflected light by the specular reflection decision unit 322 (S102: YES→S104: YES), the continuation decision unit of the control unit 3 stores a time point $T_o$ at that time (S205).

In a use time decision process P216 that is performed when reflected light is decided to be specularly-reflected light during the discharging of water (S104: NO→S115: YES), the continuation decision unit makes a decision of whether or not a time elapsed, which is the difference between the time point $T_o$ that is stored and the current time point T, is within the predetermined period of time (S217). If this time elapsed is within the predetermined period of time (S217: YES) and if the same determination has not occurred four times in a row (S218: NO), the detection decision unit 324 of the control unit 3 keeps the determination indicating the detection state even when reflected light is decided to be specularly-reflected light (S105). On the other hand, if the same determination based on the decision indicating specularly-reflected light has occurred four times in a row (S218: YES) even when the time elapsed is within the predetermined period of time (S217: YES), the detection decision unit 324 of the control unit 3 changes the determination from the determination indicating the detection state to the determination indicating the non-detection state (S129).

In the detection process according to the present exemplary embodiment, a time point at which a human body, which is a detection target, is able to be detected by reflected light other than specularly-reflected light is set as a time used as the reference for the decision. Specularly-reflected light that occurs when a time elapsed from that time point falls within the predetermined period of time (two seconds in the present exemplary embodiment) is ignored, and the determination indicating the detection state is kept without change even when specularly-reflected light becomes incident. On the other hand, in a case when a decision indicating specularly-reflected light has been made four times in a row, the determination is switched to the determination indicating the non-detection state even when the time elapsed falls within the predetermined period of time. For example, when accumulating water in both palms in order to wash face, specular reflection can occur by the rippling of a water surface or the like, and diffuse reflection can also occur. Experimental knowledge indicating that a decision indicating specularly-reflected light is less likely to occur four times or more in a row in such a situation supports an operational specification such as that described above.

The other features, operations and effects are the same as those described in the first exemplary embodiment. In the continuation decision unit 323 according to the present exemplary embodiment, the predetermined period of time is set to be two seconds. This predetermined period of time can be changed appropriately. An operation unit may be provided for adjusting this predetermined period of time so that a user is able to set the predetermined period of time according to his/her preference. The number of consecutive occurrences (the threshold value in S218) allowed for the incidence of specularly-reflected light is not limited to four stated in the present exemplary embodiment and can be changed appropriately.

While the specific examples of the present invention have been explained in detail as shown in the first and second exemplary embodiments, these specific examples merely disclose an example of technologies encompassed in the scope of the claims. Needless to say, the scope of the claims should not be interpreted in a limited manner by the features, the numerical values, and the like shown in the specific examples. The scope of the claims encompass technologies where the specific examples are modified or changed in various ways using publicly-known technologies, knowledge of those skilled in the art, and the like.

According to the present invention, an imaging element for which a CCD or a CMOS is used can be used as an imaging element that is applied to the human body detection sensor. A possible option of a method for the continuity decision unit according to the present invention to decide whether or not the state in which the detection target exists is ongoing is a decision method such as a moving object decision by moving object detection, making a decision that the state in which the detection target exists is ongoing during a predetermined period of time starting a time point at which the detection target is detected, and the like.

A continuation decision unit provided in a human body detection sensor according to a preferred embodiment of the present invention detects a temporal change of reflected light so as to decide the presence of a moving object and decides that a state in which a detection target exists is ongoing when the continuation decision unit decides that there is the moving object. Ina situation where it is decided that there is a moving object during the detection of a detection target, the detection target is very likely to have existed. Specularly-reflected light that has entered under such a situation is very likely to be reflected light from the detection target. On the other hand, for example, if reflected light is specularly-reflected light produced by a stationary object such as a bowl surface in applications in an automatic faucet, it is less likely to be decided that there is a moving object. If it is decided that the state in which the detection target exists is ongoing according to the decision indicating that there is the moving object, an erroneous determination indicating non-detection can be prevented when specularly-reflected light incidentally enters from the detection target. In the case of application to the automatic faucet according to the second embodiment, for example, in a usage situation such as a situation where water is accumulated in both palms in order to wash face, an erroneous operation where the switching to the stopping of water is immediately performed can be prevented even when specular reflection occurs by the surface of water.

A continuation decision unit provided in a human body detection sensor according to a preferred embodiment of the present invention stores, when reflected light is decided not to be specularly-reflected light by a specular reflection decision unit, a time point at which a detection target is detected and decides that a state in which the detection target exists is ongoing during a predetermined period of time starting from the time point that is stored. When the reflected light is determined not to be specularly-reflected light, it is assumed that the detection target is very likely to have existed during the predetermined period of time starting from the time point at which the detection target is detected. An erroneous determination may be induced if the state is immediately changed to a non-detection state when reflected light is decided to be specularly-reflected light even during the predetermined period of time for which such an assumption can be made. Based on a presumptive decision indicating that the state in which the detection target exists is ongoing during the predetermined period of time, an erroneous determination such as the one described above can be prevented. Since a determination regarding detection is very likely to occur repeatedly during the detection of the detection target, the predetermined period of time is preferably shifted temporally backward every time a determination indicating detection occurs.

What is claimed is:

1. A human body detection sensor for detecting a detection target provided with: an imaging unit that includes an imaging element in which pixels are arranged in a one-dimensional manner or in a two-dimensional manner; and a light-emitting unit disposed with an offset from this imaging unit, in which the imaging unit receives reflected light generated by light projected by this light-emitting unit, comprising:

a specular reflection decision unit that decides whether or not the reflected light is specularly-reflected light; and
a continuation decision unit that decides whether or not a state in which the detection target exists is ongoing,
wherein, when the reflected light is decided to be specularly-reflected light during the detection of the detection target, a determination indicating detection is kept if the result of the decision by the continuation decision unit indicates that the state is ongoing, and a determination indicating non-detection is made if the result of the decision by the continuation decision unit indicates that the state is not ongoing,
wherein the continuation decision unit is configured to detect a temporal change of the reflected light so as to decide the presence of a moving object and decide that the state in which the detection target exists is ongoing when the continuation decision unit decides that the moving object is present.

2. An automatic faucet for use with a detection target and a bowl, the automatic faucet comprising:
a faucet that discharges water into the bowl provided with a drainage port at the bottom of the bowl;

a human body detection sensor for detecting the detection target provided with: an imaging unit that includes an imaging element in which pixels are arranged in a one-dimensional manner or in a two-dimensional manner; and a light-emitting unit disposed with an offset from this imaging unit, in which the imaging unit receives reflected light generated by light projected by this light-emitting unit, comprising:

a specular reflection decision unit that decides whether or not the reflected light is specularly-reflected light; and a continuation decision unit that decides whether or not a state in which the detection target exists is ongoing, wherein, when the reflected light is decided to be specularly-reflected light during the detection of the detection target, a determination indicating detection is kept if the result of the decision by the continuation decision unit indicates that the state is ongoing, and a determination indicating non-detection is made if the result of the decision by the continuation decision unit indicates that the state is not ongoing, wherein continuation decision unit is configured to detect a temporal change of the reflected light so as to decide the presence of a moving object and decide that the state in which the detection target exists is ongoing when the continuation decision unit decides that the moving object is present; and a water supply control unit that performs the switching of discharging and stopping of water from the faucet by using a sensor signal that is output depending on whether this human body detection sensor is in a detection state or in non-detection state.

3. The human body detection sensor according to claim 1, wherein the continuation decision unit decides that there is the moving object when a temporal difference of a center of gravity of the reflected light is more than a predetermined threshold value, and wherein the predetermined threshold is a value of sub-pixel numbers.

4. The human body detection sensor according to claim 3, wherein ten sub-pixels correspond to one pixel of the imaging element.

5. The human body detection sensor according to claim 4, wherein the predetermined threshold value is five sub-pixels.

* * * * *